United States Patent [19]
Saurat et al.

[11] Patent Number: 5,615,965
[45] Date of Patent: Apr. 1, 1997

[54] DEVICE FOR INTERCONNECTING AN ELONGATE ELEMENT AND A SUPPORT FOR SAID ELEMENT

[75] Inventors: Jean Saurat, Etaples; Dominique Bigand, Stella Plage; Jean-Louis Chevalier, Merlimont Plage, all of France

[73] Assignee: Sofamor S.N.C., Rang du Fliers, France

[21] Appl. No.: 436,193

[22] PCT Filed: Nov. 10, 1993

[86] PCT No.: PCT/US93/10917

§ 371 Date: May 10, 1995

§ 102(e) Date: May 10, 1995

[87] PCT Pub. No.: WO94/11642

PCT Pub. Date: May 26, 1994

[30] Foreign Application Priority Data

Nov. 10, 1992 [FR] France .................... 92 13539

[51] Int. Cl.⁶ .................................. F16B 7/04
[52] U.S. Cl. .................. 403/24; 403/334; 403/331; 606/61; 606/73
[58] Field of Search .................. 403/334, 333, 403/331, 332, 320, 339, 340, 365, 367, 368, 381, 24; 606/73, 61, 72, 60

[56] References Cited

U.S. PATENT DOCUMENTS

| | | | |
|---|---|---|---|
| 1,167,155 | 1/1916 | Derby | 403/331 |
| 2,220,203 | 11/1940 | Branin | 403/368 X |
| 3,899,955 | 8/1975 | Selch | 403/334 X |
| 4,019,298 | 4/1977 | Johnson, IV | 403/331 X |
| 4,887,596 | 12/1989 | Sherman | 606/61 |
| 4,946,458 | 8/1990 | Harms et al. | 606/61 |
| 5,257,993 | 11/1993 | Asher et al. | 606/61 |
| 5,281,222 | 1/1994 | Allard et al. | 606/61 X |
| 5,380,326 | 1/1995 | Lin | 606/72 X |

FOREIGN PATENT DOCUMENTS

| | | | |
|---|---|---|---|
| 2697744 | 5/1994 | France | 606/61 |
| 4107480 | 9/1992 | Germany | 606/61 |

Primary Examiner—Harry C. Kim
Attorney, Agent, or Firm—Woodard, Emhardt, Naughton, Moriarty & McNett

[57] ABSTRACT

The device comprises a slide (3) so profiled as to be insertable in a support (2) in a slidable and coaxial manner with respect to an elongate element (1) and in intimate contact with the latter. This slide has two lateral lips (5) adapted to cooperate with ramps for clamping the slide and formed in the support (2), the lips and the ramps being inclined to the axis of the elongate element (1). The lips (5) are advantageously rounded and define an intermediate constricted part thereby achieving a self-clamping of each lip (5) of the slide (3) in the associated ramp of the support (2). The device supports an extremely high assembly pre-stressing without deforming or breaking, even when the prestressing is increased in an exaggerated manner, this being achieved with an overall size which is smaller than a screwed assembly of elements of a cross-shaped structure. Various applications in particular in the connection of a spinal osteosynthesis rod with a pedicular anchorage element.

17 Claims, 3 Drawing Sheets

5,615,965

DEVICE FOR INTERCONNECTING AN ELONGATE ELEMENT AND A SUPPORT FOR SAID ELEMENT

BACKGROUND OF THE INVENTION

The present invention relates to a device for interconnecting an elongate element and a support for said element which may also be elongate.

It is known that in general in mechanical construction it is desired in many fields (automobile, aeronautic, medical) to reduce the overall size of an assembly of this type while increasing its strength. For example, in the field of medical prostheses, the assembly of two parts is usually achieved by means of screws the heads of which project and consequently increase the overall size of the prosthesis resulting in considerable drawbacks for the patient.

Assemblies of dovetail type are also known but these cannot support a high assembly prestressing and do not resist large wrenching forces.

SUMMARY OF THE INVENTION

An object of the invention is therefore to provide a device for interconnecting an elongate element and a support for said element which supports a very high assembly prestressing and involves no deformation or fracture of the connection if the prestressing is increased in an exaggerated manner.

According to the invention, the connection device comprises a slide so profiled as to be capable of being slidably inserted in the support coaxially with the elongate element and in intimate contact therewith, and said slide comprises two lateral lips adapted to be cooperative with slide-clamping ramps provided in the support, the lips and the associated ramps being inclined relative to the axis of the elongate element and thereby achieving a self-clamping of each lip of the slide in the associated ramp of the support.

In one embodiment of the invention, the lateral lips of the slide are curved in the transverse direction and disposed in complementary channels of the support forming said inclined ramps.

According to another feature of the invention, the lateral lips of the slide have a rectilinear cross-sectional contour and are disposed in complementary grooves of the support forming said inclined ramps.

In a particular application, the invention provides a spinal osteosynthesis device wherein the elongate element is a rod which is smooth or has surface asperities and extends along a vertebral segment to be straightened, while its support is a screw or a hook having a U-shaped body in which a slide is slid for clamping the rod to its anchorage element constituted by the screw or hook.

Further features and advantages of the invention will be apparent from the following description with reference to the accompanying drawings which illustrate several embodiments of the invention by way of non-limitative examples.

DESCRIPTION OF THE PREFERRED EMBODIMENTS

Figure 1:
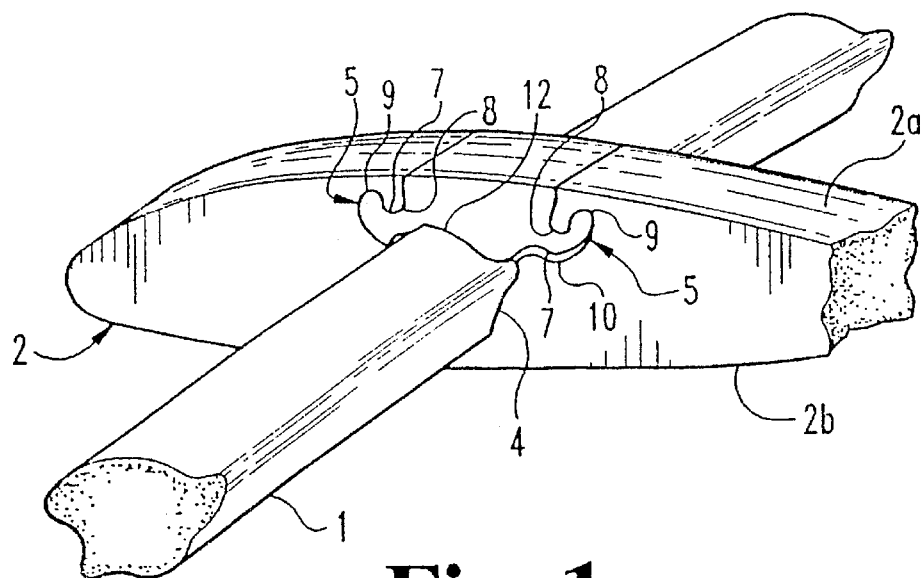
FIG. 1 is a perspective view with parts cut away of a first embodiment of the connection device according to the invention.

The device shown in FIG. 1 permits interconnecting an elongate element 1, such as a rod, and a support 2 for said element, the assembly of these two parts forming a cross-shaped structure. This device comprises a slide 3 which is so profiled as to be capable of being slidably inserted in the support coaxially with the elongate element 1 and in intimate contact with the latter.

Figure 3:
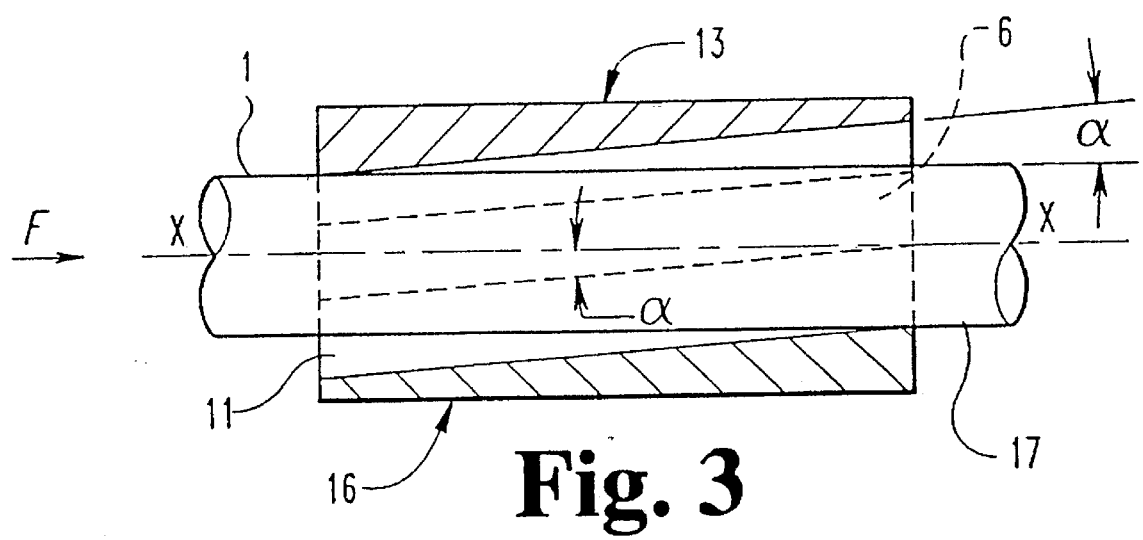
FIG. 3 is a longitudinal half-elevational view and half-sectional view taken on line 3—3 of FIG. 2.

For this purpose, there is formed in the support 2 a recess 4 on the bottom of which the elongate element 1 can bear when it extends through the support 2, the recess 4 also being so profiled as to be capable of housing the slide 3. The latter is so dimensioned that its surfaces are flush with the surfaces 2a, 2b of the support 2 when it is fully inserted in its recess 4 and bears against and clamps the element 1 to the support 2. The slide 3 has two lateral lips 5 capable of fitting by a movement in translation in complementary channels 10 in the support 2. Each channel 10, 11 defines a ramp 6 (one, 6, of these ramps is shown in FIG. 3, which section is also valid for the assembly shown in FIG. 1). The upper and lower surfaces of the channels 10, 11, their ramps 6, and the lips 5 are inclined at the same angle α to the axis X—X of the elongate element 1. In practice, the angle α is small, on the order of about 2° to 6°, and is therefore grossly exaggerated in FIG. 3 in order to facilitate the description.

The two lateral lips 5 are curved transversely in the direction toward the upper surface 2a of the support 2 and have a curvilinear contour in the same way as the remainder of the lateral surfaces of the slide 3 from which they project. Thus, each lip 5 is defined by a constricted first part 7 located in a narrow passage delimited by two confronting rounded bosses 8 laterally projecting into the recess 4, and a second enlarged and rounded part oriented toward the surface 2a. The two parts 7, 9 are received in their respective channel 10 of corresponding section formed in the support 2, the two enlarged parts 9 being placed in the corresponding lateral ramps 6. The section of the slide 3 connecting the lips 5 adjacent to the rod 1 of course has a profile 12 complementary to that of the rod 1 so as to marry up with the latter.

The assembly is achieved very simply: the rod 1 is inserted in the complementary bottom of the recess 4, then the slide 3 is slid along the surface of the rod I and inserted by sliding in the corresponding part of the recess 4. The insertion of the lips 5 in the inclined ramps 6 of course occurs from the lower end of the latter in the direction of arrow F (FIG. 3). The slide 3 is then pushed along by a suitable tool so that the lips 5 slide in the channels 10, 11 and the ramps 6 until it reaches a position of a complete clamping of the slide 3 at the end of its travel. In the last-mentioned position, the three surfaces of the slide 3 are flush with the two lateral surfaces 2b and the intervening surface 2a of the support 2.

Figure 2:
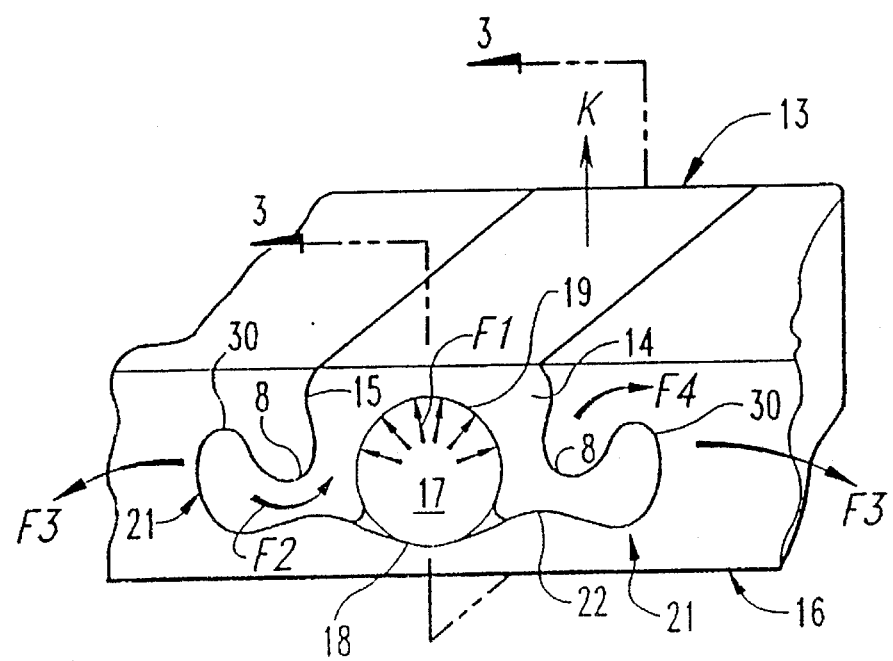
FIG. 2 is a perspective and partly sectional view of a second embodiment of the device according to the invention.

The structure shown in FIGS. 2 and 3 differs from the foregoing structure in that the lateral surfaces of the slide 13 each include a rounded boss 14 which enters a complementary recess 15 in the support 16 and the elongate element is a cylindrical rod 17. Correspondingly, the bottom 18 of the channel receiving the rod 17 is semi-cylindrical, and a complementary semi-cylindrical recess 19 is formed in the slide 13. The lips 21, which have a similar profile to the lips 5 and have enlarged end parts 30, however extend lower down relative to the rod 17, their first constricted part 22 being connected by a rounded portion to the adjacent bosses 14.

The assembling device just described has the following advantages.

After assembly, the thickness of the assembly is substantially the same as that of the support 2 or 16 owing to the fact that the upper surface of the slide 3 or 13 is substantially flush with the upper surface of the support 2, 16. The same is true of the lateral surfaces of the slide 3, 13 and support 2, 16, so that the overall size of this assembly is distinctly smaller than that of a screwed assembly.

As opposed to the screwed assembly of two profiled bodies of cross-shaped structure, or a dovetailed assembly, the assembling device according to the invention is capable of supporting, as already mentioned, a particularly high assembly prestressing without dislocation or even without deforming. Further, when it is subjected to a load, this device is unaffected by exterior stresses or forces. Indeed, the imbrication of the lips 5 or 21 in the complementary profiled channels of the support 2, 16 and the rounded and curved profile of these lips are such that even very high wrenching forces exerted in a direction transverse to the direction in which the lips 5, 21 extend cannot result in a deformation of the connection (provided of course that the materials of the two assembled bodies 1, 2 or 17, 16 and the slide 3, 13 are sufficiently strong). In the embodiment shown in FIGS. 2 and 3, the bosses 14 and their recesses 15 oppose any extraction of the slide under the effect of transverse forces, this technical result being added to that already afforded by the lips 21.

The possibility of prestressing at very high values provides an assembly system which is reliable and requires no particular precautions. A very strong or stable connection is thus obtained as concerns exterior forces exerted by the elongate element 1 on the support 2, 16, involving an axial sliding or rotation of the rod 1 or 17 in the support 2, 16.

The aforementioned technical effects are symbolically represented by the arrows F1, F2, F3, F4: the arrows F1 represent the prestressing pressure of the rod 17 on the slide 13; the arrow F2 symbolically represents the force to which the lips 21 are subjected which tends to urge them out of their recesses under the effect of the pressure F1 resulting from the prestressing, the bosses 8 of the support 16 on each side of the constricted parts 22 opposing this outward movement; the arrows F3 represent bending forces on the support 16 which tend to cause the lips 21 to move out of their channels 10, 11 (arrow F4). The bosses 8 (which constitute additional lips to the lips 21) oppose this outward movement of the lips 21.

Figure 4:
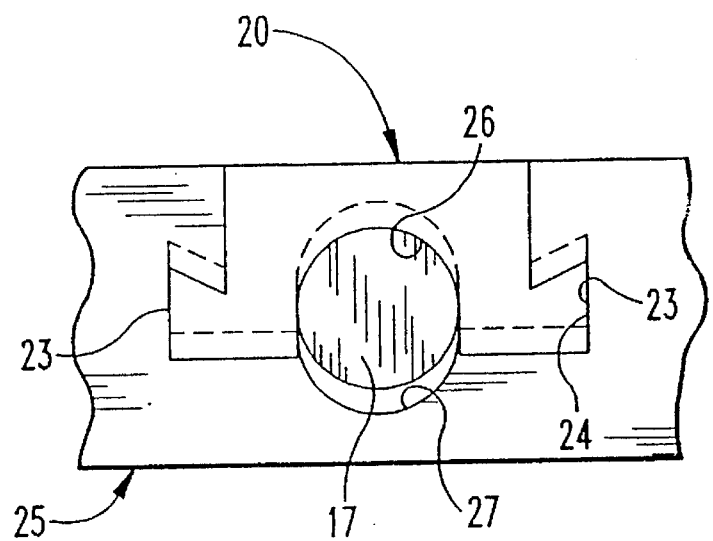
FIG. 4 is an end elevational view of a third embodiment of the connection device according to the invention.

In the modification illustrated in FIG. 4, the lateral lips 23 of the slide 20 have a rectilinear cross-sectional contour and more precisely a dovetail shape in this embodiment. The lips 23 are disposed in complementary grooves 24 in the support 25 which have, in the same way as the lips 23, a suitable inclination such as that of the ramp 6 shown in FIG. 3. Further, in order to be able to receive the cylindrical rod 17, the slide 20 has a cylindrical axial recess 26 and a recess 27 of complementary profile is provided in the bottom of the recess for the slide 20 in the support 25.

Figure 5:
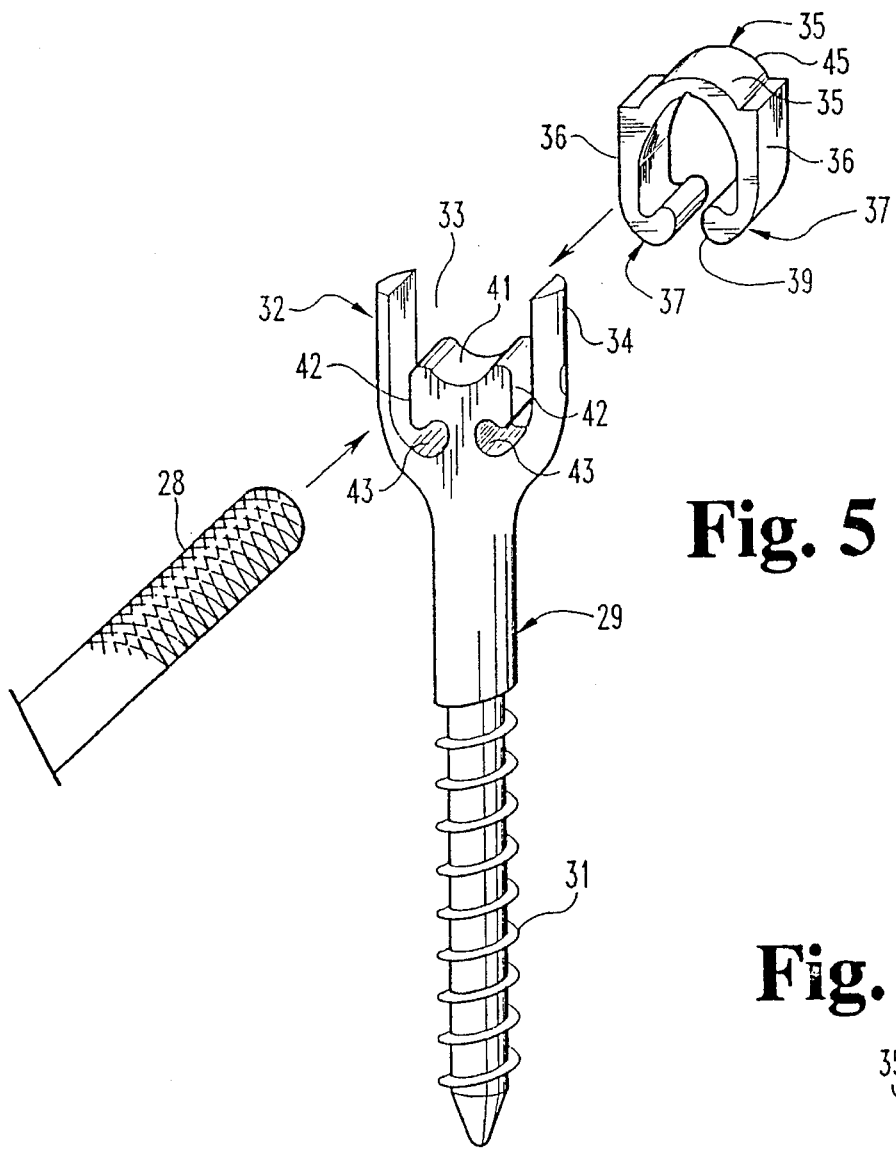
FIG. 5 is an exploded perspective view of a fourth embodiment of the invention applied to the assembly of a pedicular screw and a rod having surface asperities of a spinal osteosynthesis device.
Figure 6:
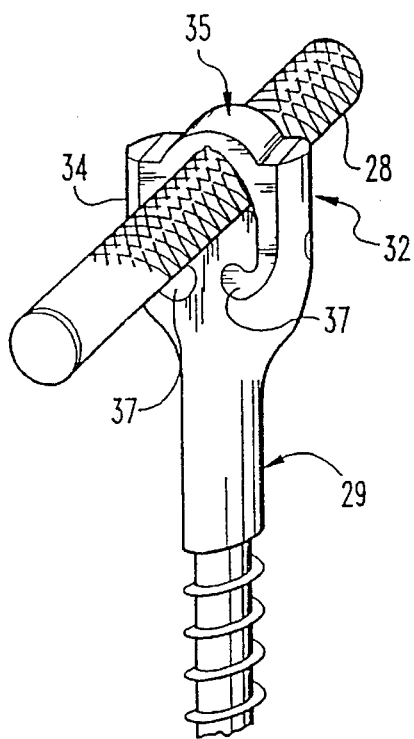
FIG. 6 is a perspective view with parts cut away of the assembly of the rod and screw shown in FIG. 5 by means of a slidable slide according to the invention.
Figure 7:
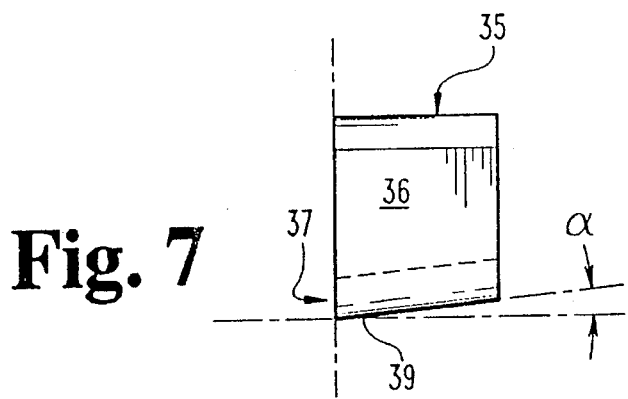
FIG. 7 is a side elevational view of the slidable slide shown in FIGS. 5 and 6.

In the device shown in FIGS. 5 to 7, the invention is applied to a connection between a spinal osteosynthesis rod 28 which has a smooth surface or a surface having asperities of the Cotrel type or knurling type, and an anchorage element 29 forming the support for the rod 28. The element 29 is, in the illustrated embodiment, a pedicular screw having a screw threaded portion 31 and a U-shaped head 32 defining a passage 33 between two branches 34. The screw 29 and the rod 28 are assembled by means of a slide 35 having a substantially U-shaped section whose parallel lateral tabs 36 are flexible so as to form a resilient clip or clamp and terminate in lips 37 which are of rounded shape, curve one toward the other, and include an enlarged end part 39 of substantially circular section. The two lips 37 are inclined at an angle α (FIG. 7) to the axis of the rod 28.

Formed between the branches 34 of the head 32 is a seat 41 of semi-circular section against which the cylindrical rod 28 bears. The seat 41 is separated from the branches 34 by slots 42 extended by channels 43 the section of which matches that of the lips 37 so as to receive the latter. The channels 43, 44 define ramps which have, in the same way as the lips 37, an inclination α (FIG. 7) to the axis of the rod 28 when the latter bears against the seat 41.

To achieve the connection between the screw 29 (which may be replaced in a modification by a pedicular hook having a U-shaped body 32) and the rod 28, the latter is placed on the seat 41, the clamp 35 is slid along the rod 28 until its tabs 36 engage the inclined ramps. 43 by resiliently spreading apart on each side of the seat 41. The clamp 35 is therefore slid along the rod until, at the end of its travel, its lips 37 are clamped against the respective ramps 43 which they completely fill.

The assembly obtained is illustrated in FIG. 6. It can be seen that the thickness of the connection is hardly increased relative to the height of the branches 34 by the curved central part 45 of the connection between the tabs 36 constituting a bridge on the surface of the rod 28.

The slide 35 is advantageously made from a soft non work-hardened material which marries up with the asperities of the rod 28 (for example constituted by diamond-shaped points) thereby affording a substantially irreversible clamping action. The lips of the slide 35 may be identical, as shown, or different.

What is claimed is:

1. In combination, an elongate spinal element with a longitudinal axis and a supporting device for use in medical prostheses, wherein said device comprising:

a spinal element support having a head portion defining a recess configured to receive the spinal element and two clamping ramps;

a slide so profiled as to be capable of being slidably inserted in said support coaxially with the elongate spinal element and in intimate contact therewith when the elongate spinal element is disposed on said support, said slide including two lateral lips cooperative with said clamping ramps; and wherein said lips and said clamping ramps are inclined relative to the longitudinal axis of the elongate spinal element when received in said recess thereby achieving a self-clamping of each of said lips of said slide in a respective one of said clamping ramps of said support when the spinal element is received in said recess and said slide is inserted in said support.

2. The combination according to claim 1, wherein said lateral lips of said slide are curved in a direction transverse to the direction of said longitudinal axis and said support defines two channels forming said inclined ramps, said channels being complementary to said lateral lips and configured to receive said lateral lips.

3. The combination according to claim 1, wherein said lateral lips of said slide have a dovetailed cross-sectional shape and said support defines two grooves complimentary to said lips and receives said lips therein.

4. The combination according to claim 1, wherein said ramps and said lips have an inclination of about 2° to 6°.

5. The combination according to claim 1, wherein said elongate spinal element is a cylindrical rod with a first radius and a semi-cylindrical axial recess for said rod is provided on the side of said slide facing toward said rod, said semi-cylindrical recess having a second radius generally equal to said first radius.

6. The combination according to claim 1, wherein said slide has two curvilinear lateral surfaces forming said lips.

7. The combination according to claim 1, wherein said support is a screw having an U-shaped head with two branches and a semi-cylindrical seat for supporting the elongate spinal element when provided between said two branches, said support defining two slots and two channels extending from said slots separating said seat from said two branches, said slide is formed by a clip having two resilient tabs having end portions constituting said lips complementary to said slots and channels and insertable in said slots and channels by sliding on the elongate spinal element received on said recess and around said seat, said channels and said lips being inclined relative to the longitudinal axis so as to clamp said elongate spinal element and said clip in position when said clip is inserted in said support with the elongate spinal element received on said seat.

8. The combination according to claim 1, wherein said support includes a vertebral engagement portion opposite said head.

9. The combination according to claim 8, wherein said vertebral engagement portion has screw threads.

10. In combination, an elongate spinal element, a support with two clamping ramps correspondingly formed from two channels defined by the support, and a connection device for use in medical prostheses, wherein said device comprising:

a slide so profiled as to be capable of being slidably inserted in the support coaxially with the elongate spinal element and in intimate contact therewith when the elongate spinal element is disposed on the support, said slide comprising two lateral lips cooperative with the clamping ramps, said lips and the clamping ramps being inclined relative to a longitudinal axis of the elongate spinal element to thereby achieve a self-clamping connection when said lips are received in the clamping ramps; and wherein each of said lips comprises a first constricted part located in a narrow passage delimited by two confronting rounded bosses on said slide, and a second enlarged and rounded part, said first and second parts of each of said lips being configured for engagement in a corresponding one of the channels of the support.

11. The combination according to claim 10, wherein said first part of each of said lips is connected to an outer surface of said slide by a rounded lateral boss which is configured to engage the support.

12. In combination, an elongate spinal rod and a spinal connection device for use in medical prostheses, wherein said device comprising:

a spinal rod support having a head portion defining a recess configured to receive the spinal rod and two clamping ramps, said support including a surface configured to bear against the spinal rod;

a slide configured for slidable insertion in said support when the spinal rod is received in said recess, said slide including two lateral lips cooperative with said clamping ramps; and wherein said lips and said clamping ramps are inclined relative to said surface of said support to thereby achieve a self-clamping of each of said lips of said slide in a respective one of said clamping ramps of said support when the spinal rod is received in said recess and said slide is inserted in said support.

13. The combination according to claim 12, wherein said ramps and said lips have an inclination of about 2° to 6°.

14. The combination according to claim 12, wherein said slide includes a pair of curvilinear lateral surfaces defining said lips.

15. The combination according to claim 12, wherein each of said lips of said slide comprises a first constricted part located in a narrow passage delimited by two confronting rounded bosses on said slide, and a second enlarged and rounded part, said support defining two channels each configured to receive said first and second parts of a corresponding one of said lips.

16. The combination according to claim 15, wherein said first part of each of said lips is connected to an outer surface of said slide by a rounded lateral boss which is inserted in a complementary recess defined by said support, insertion in said complementary recess opposing a transverse extraction of said slide.

17. The combination according to claim 12, wherein said support includes a vertebral engagement portion opposite said head portion, said vertebral engagement portion including screw threads;

said head portion of said support has two branches defining said recess therebetween, said head defines a semi-cylindrical seat between said branches for supporting the spinal rod when received in said recess, said head further defines two slots and two channels extending from said slots which separate said seat from said branches; and said slide is formed with two resilient tabs having end portions constituting profiled rounded lips complementary to said slots and channels and insertable in said slots and channels by sliding on the spinal rod, said channels and said lips cooperating to clamp the spinal rod, said support, and said slide together when the spinal rod is received on said seat and said slide is inserted in said support.

* * * * *